United States Patent [19]

Louden et al.

[11] 4,034,219
[45] July 5, 1977

[54] CLEANING SYSTEM FOR A CONTINUOUS SENSING OIL-IN-WATER MONITOR

[75] Inventors: Lester Richard Louden; Clement Auguston Blessington; Jerry Lon Beatty, all of Houston, Tex.

[73] Assignee: Dresser Industries, Inc., Dallas, Tex.

[22] Filed: Apr. 22, 1976

[21] Appl. No.: 679,297

[52] U.S. Cl. .............................. 250/301; 250/431
[51] Int. Cl.² ........................................ G01T 1/169
[58] Field of Search ........................... 250/301, 431

[56] References Cited

UNITED STATES PATENTS

| | | | |
|---|---|---|---|
| 2,732,502 | 1/1956 | Darney | 250/431 X |
| 3,731,091 | 5/1973 | Rosso et al. | 250/301 |

Primary Examiner—Archie R. Borchelt
Attorney, Agent, or Firm—Eddie E. Scott

[57] ABSTRACT

Oil and/or other material on the walls of a sample tube of an oil-in-water monitoring device is washed with a cleaning solution. In operation, a water sample is directed into the sample cell. Ultra-violet light is directed through the sample tube to the water sample. A detector detects energy emanating from the sample tube characteristic of oil. Valve means channels the cleaning solution through the sample tube to remove oil and/or other material that has accumulated on the walls of the sample tube. The valve means may be operated manually or by a programmable device.

2 Claims, 5 Drawing Figures

CLEANING SYSTEM FOR A CONTINUOUS SENSING OIL-IN-WATER MONITOR

BACKGROUND OF THE INVENTION

The present invention relates in general to the art of pollution control and more particularly to a system for improving the overall accuracy, reliability and useful lifetime of equipment for monitoring water streams containing "Oil" and/or other fluorescing products.

A summary of the state of the law applicable to oil discharges is set out in a paper by William K. Tell, Jr., Texaco, Inc., titled "Summary of Laws and Regulations Governing Spills and Discharges of Oil." The paper was given at the Joint Conference on Prevention and Control of Oil Spills, June 15–17, 1971 in Washington, D.C. and appears in the proceedings published by the American Petroleum Institute. This paper indicates that the past several years have seen a veritable explosion of environmental laws and regulations in this area. The development of new and improved oil-in-water monitoring systems is an important outgrowth of the increased awareness in this area. The present invention is directed to an oil-in-water monitoring system that uses an energy source such as ultra-violet light directed into a sample cell or tube to detect the presence of oil and/or other fluorescing products in the water being monitored. Films and other accretion on the walls of the sample tube are efficiently removed thereby preventing the accretion from causing inaccurate readings.

DESCRIPTION OF PRIOR ART

In an article titled "Characterization of Crude and Residual-Type Oils by Fluorescence Spectroscopy" by Alfred D. Thruston, Jr. and R. W. Knight, Southwest Water Laboratory, Federal Water Quality Control Administration, U.S. Department of Interior, published in Environmental Science and Technology, Volume 5, No. 1, January 1971 states that "the ability to pinpoint the source of oil in an oil spill on a beach, a river, or a harbor is vital to the enforcement of water pollution control procedures." The article indicates a method was developed to determine fluorescence intensities and wave number ratios for comparing various crude and residual-type oils. The method was applied to samples from an actual oil spill and confirmed results of infrared and metals analyses.

In U.S. Pat. No. 2,591,737 to Robert E. Souther, Jr., patented Apr. 8, 1952, a method and apparatus for the detection of crude oil in drilling muds is shown. This patent indicates that, among the methods heretofore used for detection of oil in the drilling fluid and in the cuttings, was a method of subjecting the surfaces of fluid and cutting samples to ultraviolet light which produces fluorescence of the otherwise invisible oil particles and renders them visible by their fluorescence.

Oil-in-water analysis systems are manufactued by Teledyne Analytical Instruments Company, 333 West Mission Drive, San Gabriel, California 91776. A brochure advertising their models 661R, 661C, 660R, and 660C includes the following statements. "The detection of oil by means of an ultra-violet analyzer is a practical application of Beer's Law. This law mathematically relates the concentration of oil to the amount of energy which the oil in the sample absorbs in a cell of fixed length." The system does not direct itself to the problem of accretions on the walls of the sample tube. Oil-in-water detecting equipment is also manufactured by Baird-Atomics, Inc., 125 Middlesix Turnpike, Bedfore, Massachusetts 01730 and by Wilkes Scientific Corporation, 140 Water Street, South Norwalk, Connecticut 06856.

SUMMARY OF THE INVENTION

The present invention provides a system for keeping the sample cell of an oil-in-water monitoring device clean. Sample cells of oil-in-water monitoring equipment have a tendency to become coated and cause inaccurate readings. The system is incorporated in an oil-in-water monitoring device which includes an energy source for directing energy into the sample cell and a detecting means that detects energy emanating from the sample cell. A source of cleaning solution is provided and means are provided fo transmitting the cleaning solution to the sample cell in place of the sample fluid for selected periods at selected intervals. The above and other features and advantages of the present invention will become apparent from a consideration of the following detailed description of the invention when taken in conjunction with the accompanying drawings.

DETAILED DESCRIPTION OF THE INVENTION

Figure 1:
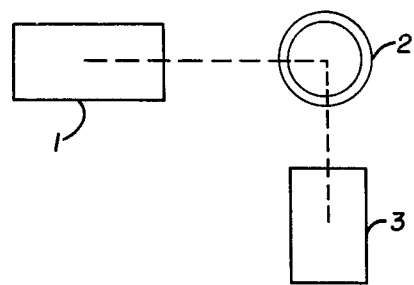
FIG. 1 illustrates an oil-in-water monitoring system.

Referring now to FIG. 1, an oil-in-water monitoring system generally consisting of a light source 1, a sample cell 2 and a detector 3 is illustrated. Light from light source 1 is directed into sample cell 2 and light energy emanating from sample cell 2 is monitored by detector 3 which acts to detect light energy characteristic of oil. For example, light source 1 may be a mercury vapor lamp which directs light energy through an excitation filter with a mask which directs the light energy into the sample tube 2. The detector 3 may be a photo-multiplier detector positioned to receive light energy emanating from the sample tube 2. The detector 3 may include a mask which directs the light energy emanating from sample tube 2 though an emission filter to the photo-multipler detector. The detector 3 acts to detect light energy characteristic of oil. Oil-in-water monitoring systems of this type were discussed in the foregoing Description of Prior Art section.

A fundamental problem with prior art oil-in-water monitoring systems has been discovered in that an oil film and a deposit such as calcium carbonate tend to build up on the sides of the sample tube and inaccurate readings are produced. The exact cause of the deposit is not known although it may result from the light energy interacting with chemical constituents of the sample being monitored. The present invention provides a system incorporated in an oil-in-water monitoring system that substantially reduces and/or eliminates inaccuracies created by the accretion on the walls of the sample tube.

Figure 3:
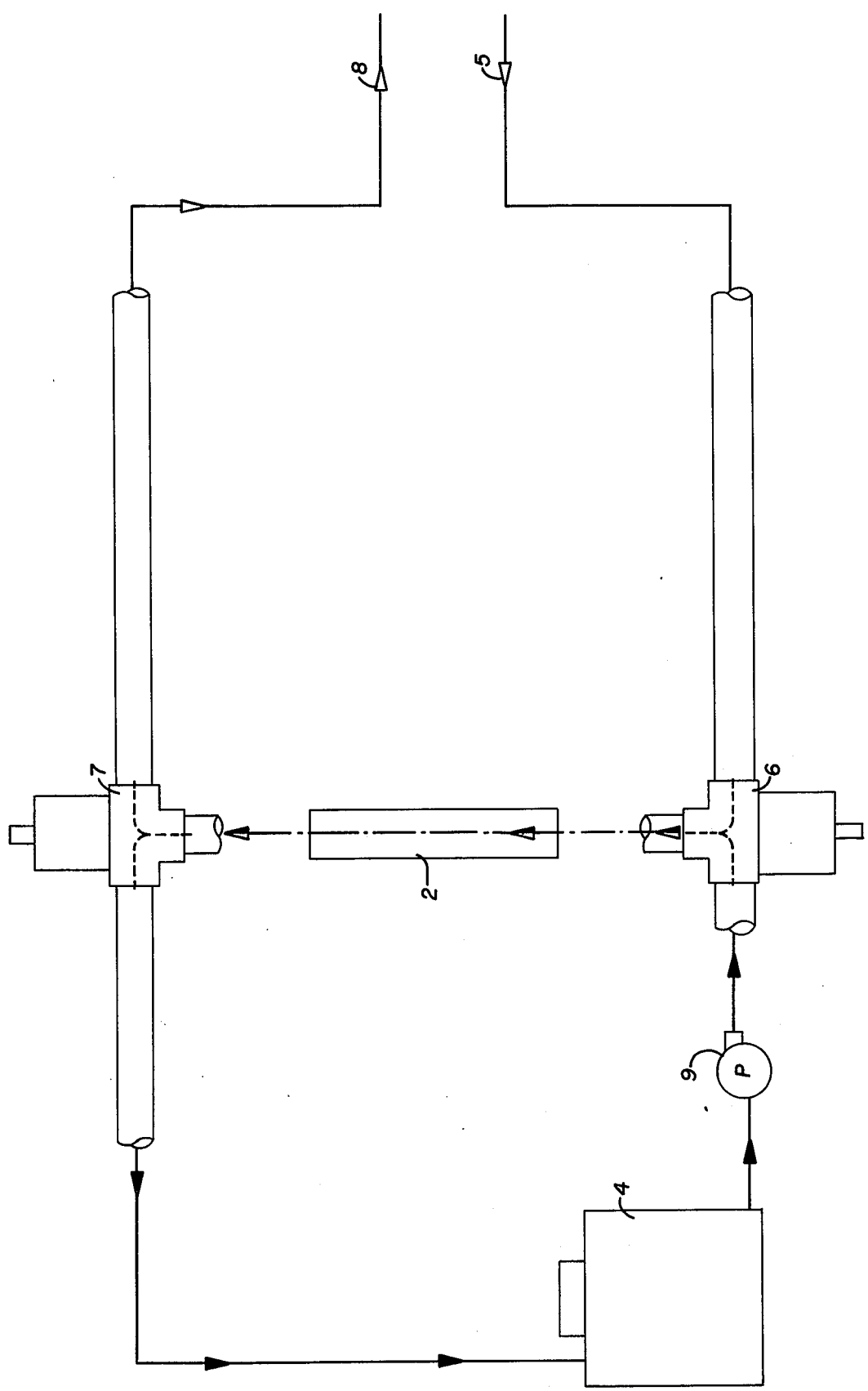
FIG. 3 is a schematic flow diagram of a cleaning system for the oil-in-water monitoring system shown in FIG. 1.

Referring now to FIG. 3, a flow diagram of a system for cleaning the sample tube 2 of the oil-in-water monitoring system shown in FIG. 1 is illustrated. A cleaning solution from tank 4 is circulated through the sample tube 2 during a wash cycle. During the normal monitoring operation the water being monitored is channeled from a source at 5 though a three-way valve 6 into the sample tube 2. The water being monitored travels from the sample tube 2 through a three-way valve 7 and exits from the system at 8. At selected intervals the monitoring is interrupted to place the system in the wash cycle. Valves 6 and 7 are actuated to shut off flow of the water being monitored from the source at 5 and let the cleaning solution from tank 4 be pumped by pump 9 through the three-way valve 6 into the sample tube 2. The cleaning solution removes the accretion on the walls of the sample tube 2 and is directed through three-way valve 7 back to tank 4.

According to the present invention, it has been discovered that continuously accurate readings may be obtained by periodically circulating the cleaning solution from tank 4 through the sample tube 2. The accretion of oil and/or other deposits on the sides of the sample tube 2 are removed and accurate readings are obtained by the oil-in-water monitoring system. For example, successful results have been obtained with a cleaning solution including a detergent and an organic phosphate type scale inhibitor. The detergent component may consist of a modified coconut alkanolamide, ethylene glycol monobutyl ether, monoalkyl phenol [10½ mole ETO] and water. The organic phosphate type scale inhibitor component may consist of a neutralized blend of phosphoric acid, polyacrylic acid and water. The approximate relationship of the detergent component to the organic phosphate type scale inhibitor component is two parts detergent to one part organic phosphate type scale inhibitor.

Figure 2:
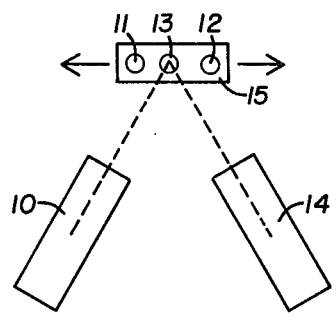
FIG. 2 illustrates another oil-in-water monitoring system.

Referring now in FIG. 2, another embodiment of an oil-in-water monitoring system is illustrated. This embodiment allows a water sample to be continuously monitored. Light from a light source 10 is directed selectively into either a first sample tube 11 or second sample tube 12 or into a standard 13. Light emitted from the respective first sample tube 11, second sample tube 12 or standard cell 13 is directed to a detector 14. The sample holder unit 15 is adapted to be moved so that the light beam is directed into either the first sample tube 11, the second sample tube 12 or the standard 13. Light emanating from the respective sample tube is directed to a detector 14. The detector 14 indicates the presence of oil by detecting light wave lengths characteristic of oil. The system utilizes a sampling cycle and a wash cycle for each sample tube and by using two sample tubes allows continuous uninterrupted monitoring of the water sample.

As previously mentioned, a fundamental problem with prior art oil-in-water monitoring systems has been discovered in that an oil film and a deposit such as calcium carbonate tend to build up on the sides of the sample tubes and inaccurate readings are produced. The exact cause of the deposit is not known although it may result from the ultra-violet light interacting with chemical constituents of the sample being monitored. The present invention incorporates a wash cycle in an oil-in-water monitoring system thereby eliminating inaccuracies created by accretion on the sample tube and at the same time providing continuous monitoring capability.

Figure 4:
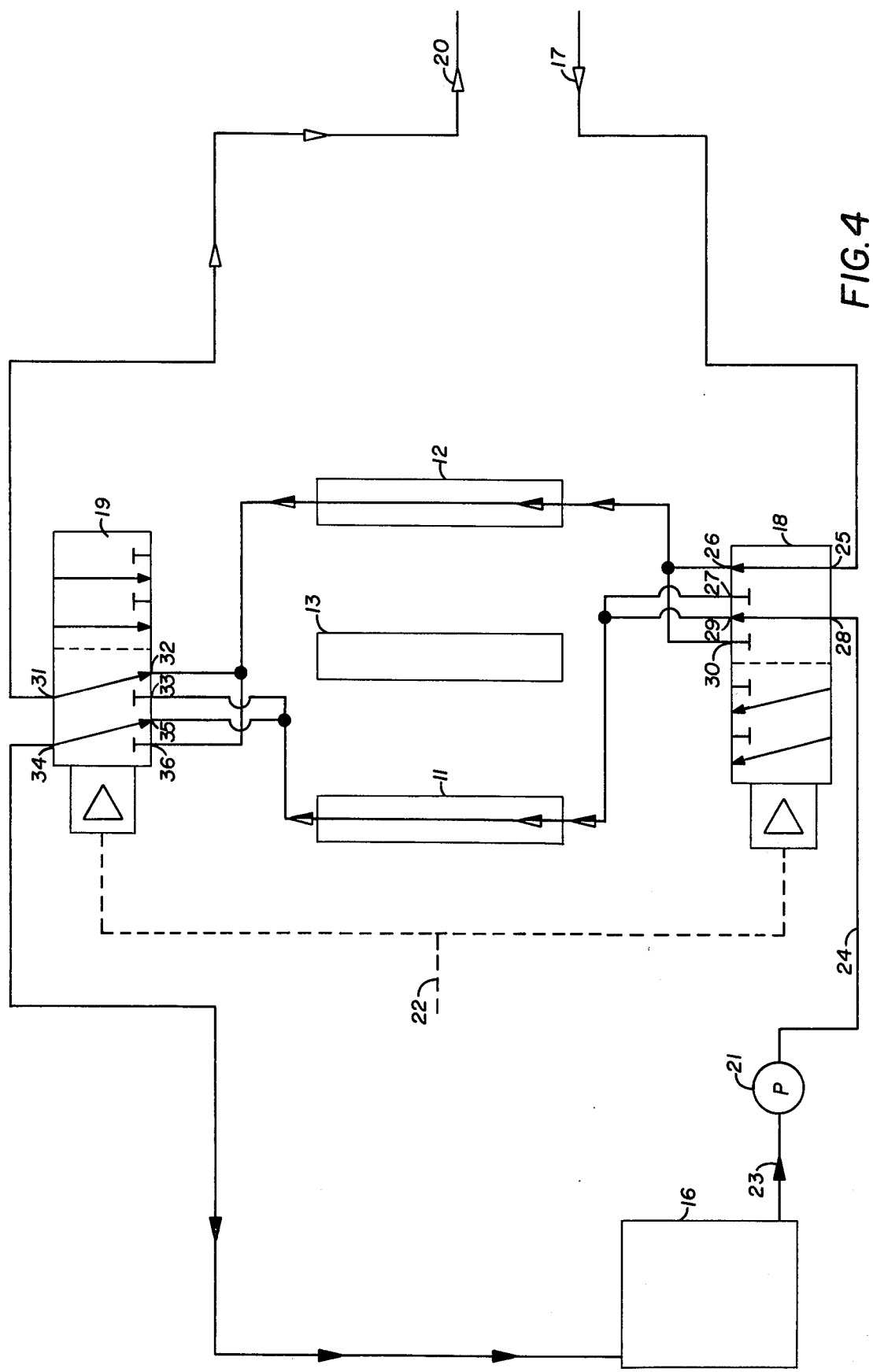
FIG. 4 is a schematic flow diagram of a cleaning system for the oil-in-water monitoring system shown in FIG. 2.

Referring now to FIG. 4, a flow diagram is shown wherein a wash solution from tank 16 may be alternately circulated through either the first sample tube 11 or the second sample tube 12. Simultaneously with the wash solution being circulated through one sample tube the water sample is directed through the other sample tube. As shown in FIG. 4, the water being monitored in channeled from a source at 17 though a valve 18 into the second sample tube 12. The water sample travels from the sample tube 12 through multi-port valve 19 and exits from the system at 20. Simultaneously, the wash solution is pumped from tank 16 by pump 21 and directed through valve 18 into the first sample tube 11. The wash solution removes accretion on the walls of the first sample tube 11 and travels through valve 19 back to tank 16. At periodic intervals, valves 18 and 19 are actuated by common actuator 22 to direct the water being monitored through the first sample tube 11 and the cleaning solution through the second sample tube 12. The pump 21 is connected to tank 16 by line 23 and to valve 18 by line 24.

Valve 18 includes a port 25 connected to receive the water sample to be monitored. The water being monitored will be directed out of valve 18 though either port 26 in the first position or port 27 in the second position. The valve 18 includes a port 28 connected to the source of cleaning solution in tank 16. The cleaning solution will be directed from valve 18 through either port 29 in the first position or 30 in the second position. Valve 19 includes a port 31 connected to discharge the water being monitored. The water being monitored will be directed into valve 19 through either port 32 in the first position or 33 in the second position. The valve 19 includes a port 34 connected to return the cleaning solution to tank 16. The cleaning solution will be directed into valve 19 through either port 35 in the first position or port 36 in the second position.

Actuator 22 may be a common actuator to start pump 21, to change valve 18 and to change valve 19 simultaneously or may be a group of separate actuators or any desired combination. It may be manually operated or it may be a programmable device to actuate each in a predetermined sequence based on any desired parameter such as time or fluid volume. Generally, it is desirable to have valve 19 actuated slightly later than valve 18 to prevent passing the water being monitored to the cleaning solution tank. The standard sample cell 13 is included to provide calibration standard. No flow is provided through the standard cell 13.

Figure 5:
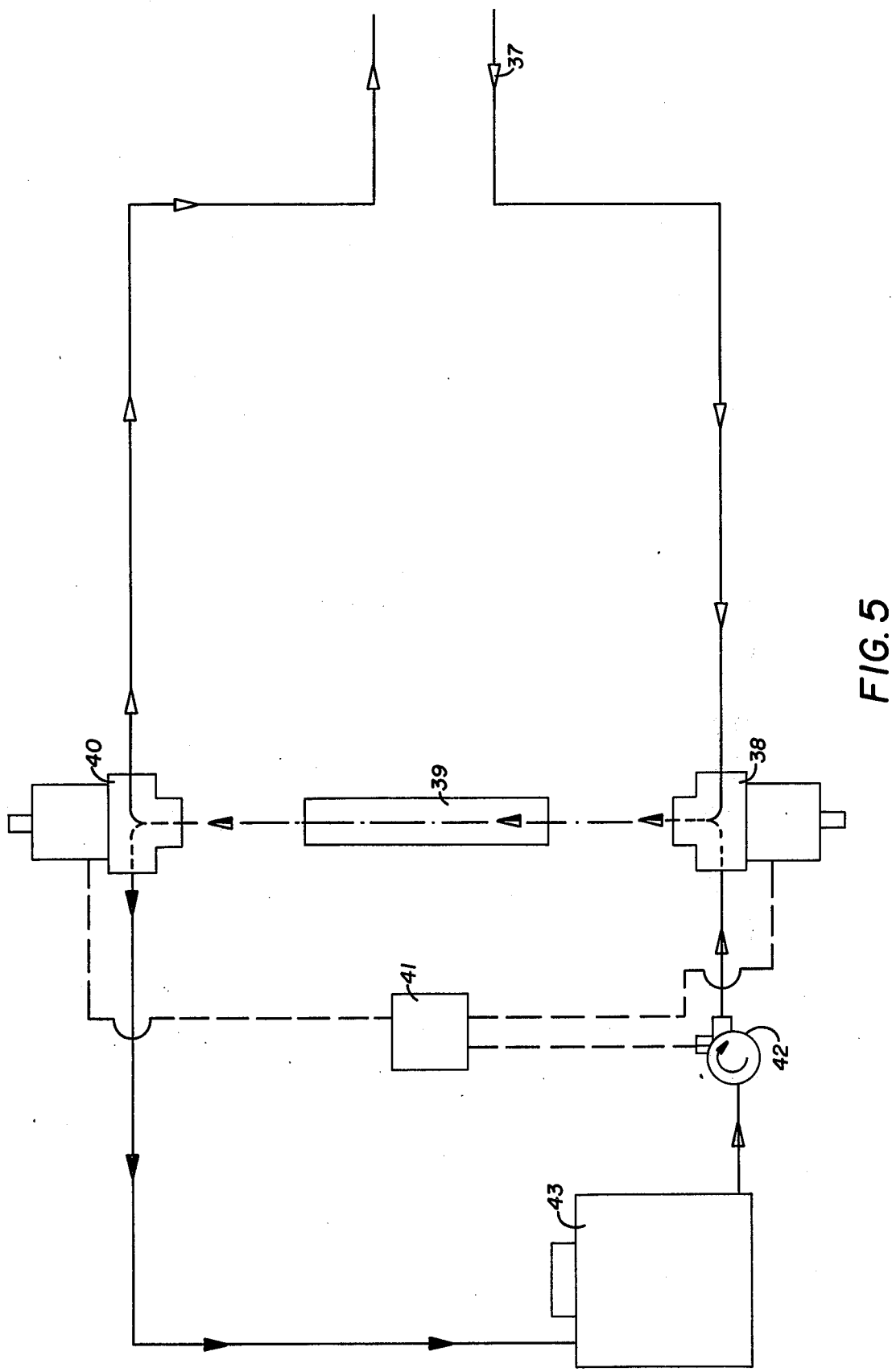
FIG. 5 illustrates another cleaning system for an oil-in-wter monitoring system.

Referring now to FIG. 5, another embodiment of a system for cleaning a sample tube of an oil-in-water monitoring system is illustrated. A cleaning solution from tank 43 is circulated through a sample tube 39 during a wash cycle. During the normal monitoring operation, the water being monitored is channeled from a source 37 through a three-way valve 38 into the sample tube 39. The water being monitored travels from the sample tube 39 through a three-way valve 40 and exits from the system. At selected intervals, the monitoring is interrupted to place the system in a wash cycle. Valves 38 and 40 are actuated to shut off flow of the water being monitored from the source at 37 and let the cleaning solution from tank 43 be pumped by pump 42 though the three-way valve 38 into the sample tube 39. The cleaning solution removes the accretion of the walls of the sample tube 39 and is directed through three-way valve 40 back into tank 43. The valves 38 and 40 are actuated by a programmable device 41. The programmable device 41 is a sequencing clock that will actuate valves 38 and 40 and start pump 42 on a preselected sequence. It will be appreciated that other state of the art programmable devices may be used in place of device 41. The valve 40 is actuated slightly later than the actuation of valve 38 to prevent channeling the water being monitored into the cleaning solution tank. The time delay for actating valve 40 is the length of time required for fluid to travel from valve 38 to valve 40.

The programmable device 41 will allow the water being monitored to be circulated through the sample tube 39 for a preselected period of time, say for example, six hours. At that time, the programmable device 41 will actuate valve 38 to block flow from the source of the water being monitored 37 and intiate flow of cleaning solution from tank 43. At the same time, the prgrammable device 41 will actuated pump 42 to begin circulating cleaning solution from tank 43 through sample tube 39. Since the sample tube and the flow lines between valves 38 and 40 are at this point filled with the water being monitored, the valve 40 is not actuated, but allows the water being monitored to be circulated from the system. The probrammable device 41 delays actuation of valve 40 until the interface between the cleaning solution and the water being monitored reaches valve 40. The valve 40 is then actuated to channel only the cleaning solution back to tank 43.

The embodiment of the invention in which an exclusive property or privilege is claimed are defined as follows:

1. Apparatus for sensing oil in a water sample, comprising:
   a sample tube;
   light source means for directing light energy into said sample tube;
   detector means for detecting light energy characteristic of oil emanating from said sample tube;
   sample conduit means for channeling said water sample, said sample conduit means having a sample outlet end;
   a source of cleaning solution;
   cleaning solution conduit means connected to said source of cleaning solution, said cleaning solution conduit means having a cleaning solution outlet end; and
   valve means for directing said water sample and said cleaning solution through said sample tube, said valve means having a first port connected to said sample outlet end of said sample conduit, a second port connected to said cleaning solution end of said cleaning solution conduit, a third port in communication with said sample tube, and means for selectively blocking said second port and allowing said water sample to be directed thorugh said sample tube and selectively blocking said first port and allowing said cleaning solution to be directed through said sample tube.

2. Apparatus for continuously detecting the presence of oil in a water sample, comprising:
   a first sample tube;
   a second sample tube;
   and energy source for directing energy into one of said first sample tube and second sample tube;
   detecting means for detecting energy characteristic of oil coming from one of said first sample tube and second sample tube;
   cleaning solution in a source of cleaning solution;
   valve means for selectively directing said water sample through said first sample tube and simultaneously directing said cleaning solution from said source of cleaning solution though said second sample tube and selectively directing said water sample through said second sample tube and simultaneously directing said cleaning solution from said source of cleaning solution through said first sample tube.

* * * * *